United States Patent
Schenk

Patent Number: 6,048,344
Date of Patent: Apr. 11, 2000

[54] THREADED WASHER AND BONE SCREW APPARATUS

[75] Inventor: Beat Schenk, Paoli, Pa.

[73] Assignee: Synthes (U.S.A.), Paoll, Pa.

[21] Appl. No.: 09/193,925

[22] Filed: Nov. 17, 1998

Related U.S. Application Data

[62] Division of application No. 08/591,229, Jan. 18, 1996.

[51] Int. Cl.⁷ .................................................. A61B 17/56
[52] U.S. Cl. ............................................ 606/73; 606/61
[58] Field of Search .............................. 606/73, 72, 61, 606/60, 76, 77, 104

[56] References Cited

U.S. PATENT DOCUMENTS

| | | |
|---|---|---|
| Re. 33,348 | 9/1990 | Lower . |
| 3,051,169 | 8/1962 | Grath . |
| 4,456,005 | 6/1984 | Lichty . |
| 4,716,893 | 1/1988 | Fischer et al. . |
| 4,988,351 | 1/1991 | Paulos et al. . |
| 5,084,050 | 1/1992 | Dranert . |
| 5,098,434 | 3/1992 | Serbousek . |
| 5,108,443 | 4/1992 | Branemark . |
| 5,156,616 | 10/1992 | Meadows et al. . |
| 5,211,647 | 5/1993 | Schmieding . |
| 5,242,447 | 9/1993 | Borzone . |
| 5,370,662 | 12/1994 | Stone et al. . |
| 5,456,685 | 10/1995 | Huebner . |
| 5,470,334 | 11/1995 | Ross et al. . |
| 5,520,690 | 5/1996 | Errico et al. . |
| 5,531,746 | 7/1996 | Errico et al. . |
| 5,544,993 | 8/1996 | Harle . |
| 5,569,251 | 10/1996 | Baker et al. . |

FOREIGN PATENT DOCUMENTS

| | | |
|---|---|---|
| 0 194 409 | 9/1986 | European Pat. Off. . |
| 0 263 938 | 4/1988 | European Pat. Off. . |
| 2 674 119 | 9/1992 | France . |

*Primary Examiner*—Michael Buiz
*Assistant Examiner*—Jonathan D. Goldberg
*Attorney, Agent, or Firm*—Fish & Richardson P.C.

[57] ABSTRACT

A threaded washer with a central bore for use with a bone screw is disclosed. The washer is threaded into a counterbore extending below the bone surface and into cancellous bone material. The external washer threads are tapered to provide improved purchase. The bone screw is inserted through the central bore of the washer and threaded into the fragment beyond the fracture. The washer provides improved compressive forces while permitting the bone screw head to be located beneath the bone surface.

13 Claims, 6 Drawing Sheets

THREADED WASHER AND BONE SCREW APPARATUS

This is a divisional of copending application Ser. No. 08/591,229, filed Jan. 18, 1996.

FIELD OF THE INVENTION

The invention relates generally to the use of small screws in the reduction and compression of fractures and nonunions where the bones or bone fragments are small. These screws must provide sufficient stability and compression along the fracture line to promote healing. For intra-articular applications, the screw head must not protrude above the bone surface in order to avoid interference with joint movement and with surrounding tissue. The invention specifically relates to the use of a washer with external tapered threads to position the head of the small screw securely in the layer of cancellous material below the surface of the bone.

BACKGROUND OF THE INVENTION

In orthopedics, successful treatment of nonunion and fracture of small bone fragments often involves the use of small screws. These screws are installed through both fragments in a direction substantially normal to the fracture plane. The small screw must compress the fragments sufficiently to promote healing.

Fractures resulting in small bone fragments often occur in bones adjoining intra-articular regions, such as the scaphoid, other carpal bones, ends of long bones, and bones of the spine. It is important in these applications that the head of the bone screw does not protrude from the outer surface of the bone, where the screw head could interfere with joint movement or damage surrounding tissue during articulation.

Standard small bone screws having threads only on the leading portion of the shank have been tried in this application. These screws are threaded into pre-drilled holes until the head contacts the outer fragment. The screw is then turned until a force is generated compressing the fragments between the screw head and the threads, which engage the inner fragment. In intra-articular applications, the pre-drilled hole must be countersunk to prevent the head of the screw from protruding from the bone surface. The depth of this counterbore often exceeds the thickness of the relatively thin bone cortex and penetrates to the softer cancellous bone below. When tightened, the small screw head can sink further into the cancellous bone, providing insufficient compressive forces for proper union of the fragments.

Another approach to this problem is disclosed in U.S. Pat. No. 4,175,555 to Herbert, which shows a small, headless screw utilizing threads of different pitch at the leading and trailing ends. The differential in pitch draws the bone fragments together as the screw is tightened. Because the screw head is replaced by the threads on the trailing end, the screw does not protrude from the bone and does not require countersinking. The threads on the trailing portion of the screw provide some purchase in the cancellous bone material. These screws, however, provide insufficient compression in many applications. Furthermore, a surgeon installing the screw must exercise care in starting each set of threads into the bone so that proper fracture reduction and compression occur simultaneously with the screw head reaching the proper depth. Otherwise, optimum fracture compression may occur too early, with the trailing end protruding from the bone, or too late, with the trailing screw threads engaging part of the inner fragment.

U.S. Pat. No. Re. 33,348 to Lower discloses a hip screw with an unthreaded shaft section and a leading threaded portion. A threaded sleeve member is retained on and slidable along the unthreaded shaft portion. The threads of the sleeve are designed to engage the relatively thick bone cortex of the femur. The threads on the leading portion and on the sleeve have different pitches. The assembled screw is installed as a unit, with compressive forces being generated as a result of the pitch differential as in Herbert '555. The two-piece design permits the unthreaded shaft section of the screw to back out through the sleeve member when bone absorption occurs, solving the problem of prior hip screws being forced in the opposite direction, into the hip joint capsule.

A method frequently used for the installation of small bone screws is to first install a guide wire in the bone in the location and orientation decided upon for the screw. The wire passes through the surrounding soft tissue, providing a guide for tools, such as screwdrivers, reamers and drills, and a guide for the orthopedic implants, such as screws and washers. Tools and implants used in such a procedure are cannulated, i.e. provided with a central bore through the long axis for placement over the wire.

SUMMARY OF THE INVENTION

It is an object of the present invention to provide a threaded washer for countersinking a small bone screw below the surface of an outer bone fragment without compromising the compressive forces that the bone screw can exert between the inner and outer fragments.

It is a further object to provide a threaded washer that provides sufficient purchase in cancellous bone to support the head of a small bone screw.

It is a further object of the invention to provide a threaded washer to support a small bone screw, wherein the washer thread is tapered to increase the purchase in cancellous bone and to prevent the washer from advancing while inserting the screw.

It is a further object of the invention to provide a method for immobilizing and compressing bone fragments using a threaded washer that is countersunk into the cancellous material of the outer fragment to support the head of a small bone screw beneath the surface of the fragment in an intra-articular region.

In accordance with the invention, the noted drawbacks of existing means of installing small bone screws are overcome by use of a threaded washer having an external, tapered thread with a thread form designed for purchase in cancellous material, a central bore for insertion of the bone screw, and provision for receiving a driving means such as a hexagonal drive.

In one aspect of the invention, the threaded washer is used with a cannulated screw. A guide wire is first inserted into the bone at the location selected for the screw. A cannulated, reamer is then used to form a hole sufficiently deep to accommodate the threaded washer below the surface of the bone. The threaded washer is then inserted using a cannulated driver, and driven into the cancellous bone material until the tapered thread is fully engaged in the hole. The cannulated screw is then installed through the central bore of the threaded washer, and driven using a cannulated driver until the head of the screw contacts the threaded washer. Further turning of the cannulated screw has no effect on the position of the tapered washer, but serves to reduce the fracture and apply compressive forces across the fracture plane.

The advantages of the threaded washer according to the invention reside partly in its universal applicability, since it can be used together with standard cannulated screws.

The threaded washer according to the invention can be used in applications where the bone screw must be inserted into the bone through a wall adjoining an intra-articular region, as is typically the case in scaphoid fractures. In such applications, it is important to countersink the head of the screw into the bone to avoid interference with joint articulation. This must be done without compromising the compressive forces applied across the fracture plane. With its improved purchase in the cancellous material surrounding the counterbore, the threaded washer of the invention provides this added compressive strength while still allowing the use of miniature screws with small screw heads.

Preferably the threaded washer and the bone screw have the same pitch. An advantage of the threaded washer over the use of existing screws having a pitch differential between the leading and trailing threads is that fracture reduction is controlled independently of the depth of the screw head beneath the bone surface. In the present invention, once the head of the bone screw contacts the threaded washer, all further rotation of the screw reduces the fracture or applies compressive forces across the fracture plane, without changing the depth of the screw head beneath the bone surface.

DESCRIPTION OF THE DRAWINGS

The invention will be disclosed more fully in connection with the accompanying drawings in which.

DETAILED DESCRIPTION

Figure 1:
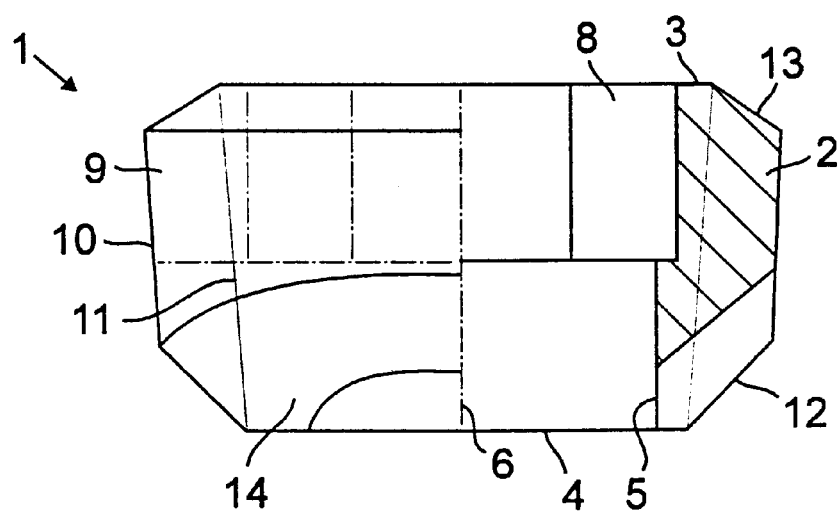
FIG. 1 is a side elevation view in partial cross section of a threaded washer according to the invention.
Figure 2:
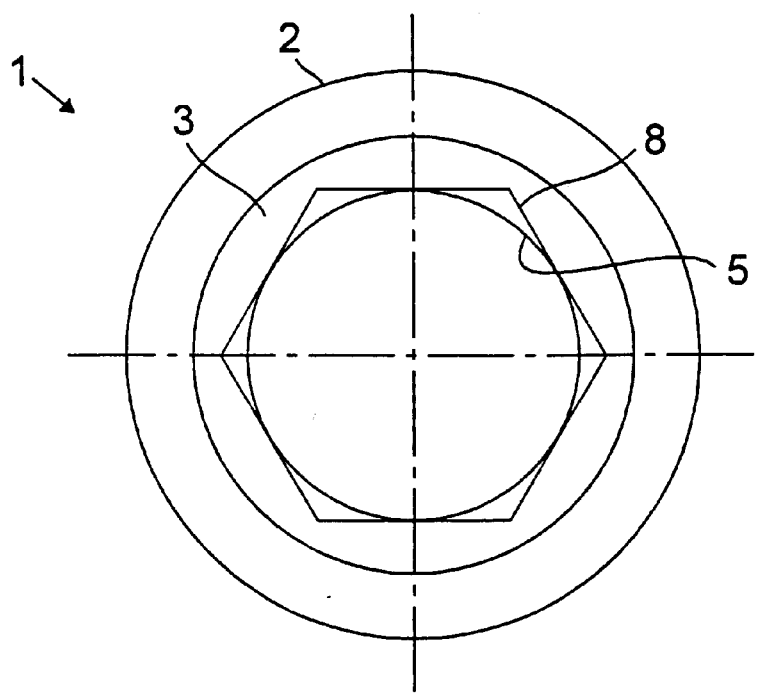
FIG. 2 is a top view of the threaded washer of FIG. 1.

FIGS. 1 and 2 show a threaded washer 1 according to the invention. As best seen in FIG. 1, the threaded washer 1 comprises a hollow cylindrical body 2 with a trailing edge 3 and a leading edge 4. A central unthreaded bore 5 extends along a central axis 6 of the cylindrical body 2.

In the embodiment shown in FIGS. 1 & 2, a hexagonal socket 8 is provided in the central bore 5 at the trailing edge 3 for driving the threaded washer with a hexagonal drive (not shown). Those skilled in the art will recognize that other driving means, such as a double pin or a slot, could be used.

A tapered, external thread 9 is provided on the outer surface of the hollow cylindrical body 2. The thread form, including the tip 10 and root 11, is gradually reduced in size from the trailing edge 3 to the leading edge 4, to form a taper. In one embodiment of the invention, the thread 9 is tapered 4.5 degrees per side. The taper provides increased purchase in cancellous bone material, and prevents the threaded washer from advancing while turning a bone screw that has been inserted through bore 5.

Figure 3:
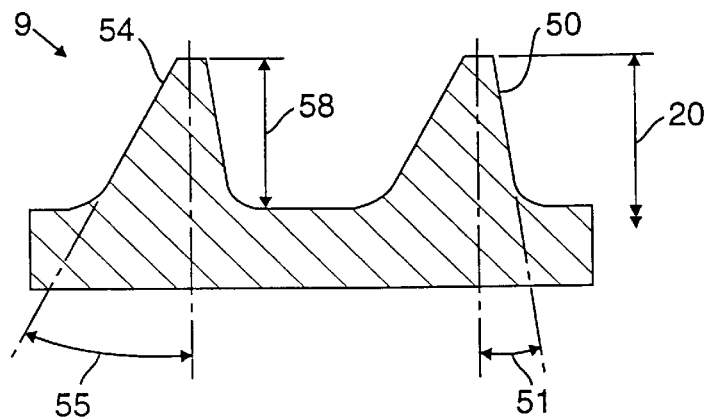
FIG. 3 is a longitudinal section through a portion the threads of the threaded washer.

In the preferred embodiment, the tapered thread 9 of the washer has cutting flutes 14, shown in FIG. 1, to make the washer 1 self-tapping. The form of the thread 9 is a cancellous thread form; that is, a form designed for purchase in cancellous bone. FIG. 3 shows a cancellous thread form used in one embodiment of the invention. The thread leading face 50, which transfers the compressive force between the threaded washer and the surrounding cancellous bone tissue, has a small leading face angle 51, for example 10 degrees. The trailing face 54 has a trailing face angle 55 greater than the leading face angle, for example 30 degrees. This embodiment has a major diameter 20 of 5.5 mm and a whole tooth depth 58 of 0.625 mm. It will be understood, however, that the invention is in no way limited to this or any other thread configuration.

External chamfer 12, shown in FIG. 1, is provided on the tapered thread 9 where it intersects the leading edge 4, in order to facilitate insertion of the threaded washer, as described below. A second external chamfer 13 is provided on the trailing edge of the washer to break the sharp corner.

In one embodiment, the threaded washer of the invention is fabricated from a biologically inert metal such as titanium, a titanium alloy, or an implant quality stainless steel, for example ASTM-316L. A metallic washer and screw are often removed in a subsequent surgical procedure after the fracture has healed. For example, the washer and screw may be removed to relieve discomfort caused by continued bone compression across the healed fracture plane.

In an alternative embodiment, the washer may be fabricated from a bio-absorbable material. In this case, no subsequent implant removal procedure is contemplated, and bone material is permitted to form around the metallic screw as the washer is absorbed by the patient's system. Furthermore, compression on the bone fragments is gradually reduced as the washer is absorbed.

Resorbable or degradable materials that may be used for fabricating the washer include ceramics based, for example, on tricalcium phosphate, hydroxyapatite, calcium carbonate or combinations thereof.

Other materials which can be used for the washer according to the invention include polymers such as highly purified polyhydroxyacids, polyamines, polyaminoacids, copolymers of amino acids and glutamic acid, polyorthoesters, polyanhydrides, amides, polydioxanone, polydioxanediones, polyesteramides, polymalic acid, polyesters of diols and oxalie and/or succinic acids, polycaprolactone, copolyoxalates, polycarbonates or poly (glutamicco-leucine). Preferably used polyhydroxyacids comprise polycaprolactone polylactides in their various chemical configuration [e.g. poly(L-lactide), poly(D-lactide), poly(L/D-lactide), poly(L/DL-lactide)], polyglycolide, copolymers of lactide and glycolide of various compositions, copolymers of said lactides and/or glycolide with other polyesters, copolymers of glycolide and trimethylene carbonate, poly(glycolide-co-trimethylene carbonate), polyhydroxybutyrate, polyhydroxyvalerate, copolymers of hydroxybutyrate and hydroxyvalerate of various compositions.

Further materials to be used as additives are composite systems containing resorbable polymeric matrix and resorbable glasses and ceramics based, for example, on tricalcium phosphate, hydroxyapatite, and/or calcium carbonate admixed to the polymer before processing.

Figure 4:
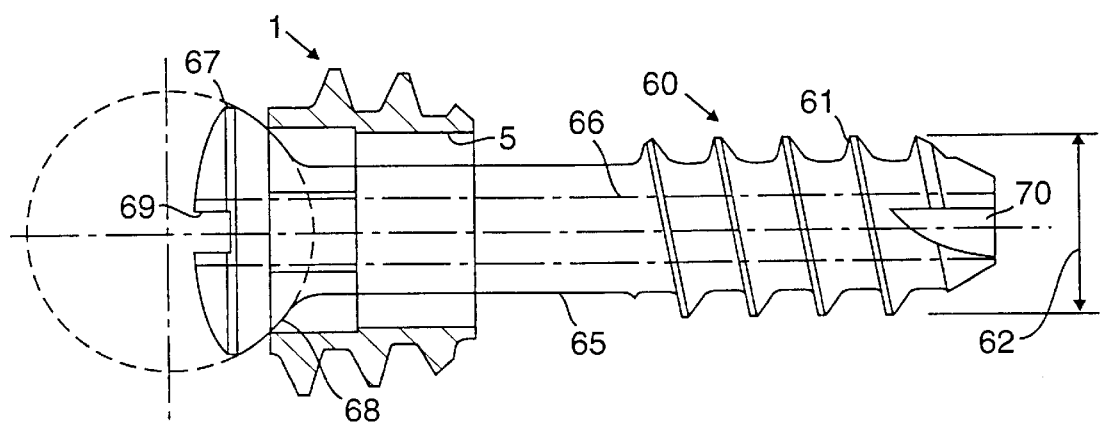
FIG. 4 is a side elevation sectional view of a threaded washer according to the invention with a cannulated screw shown in the installed position.

FIG. 4 shows a threaded washer 1 of the invention with a cannulated screw 60. The screw shown in FIG. 4 is a 2.7 mm cannulated screw sold by Synthes (USA), the assignee of the present invention. Those skilled in the art will recognize that other standard bone screws, both cannulated and non-cannulated, can be used with the threaded washer of the invention.

The bone screw 60 has a thread 61 designed for purchase in cancellous bone material. The bone screw thread 61 has a major diameter 62. The central bore 5 of the threaded washer 1 is slightly larger than the major diameter 62 of the bone screw threads, so that bone screw 60 can be inserted into the threaded washer 1 without contacting the internal wall of the washer. In the embodiment shown in FIG. 4, the central bore 5 of the washer 1 is approximately 0.3 mm larger than the major diameter 62 of the bone screw thread 61.

Bone screw head 67 has a spherical undersurface 68. The spherical undersurface tangentially engages the corners formed by the hexagonal socket 8 and the top edge 3. Between the bone screw thread 61 and the bone screw head 67 is an unthreaded shaft portion 65. Self-drilling flutes 70 at the distal end of the bone screw thread 61 permit the screw to be inserted without pre-drilling or tapping.

The cannulated bone screw 60 shown in FIG. 4 furthermore has a central bore 66 for receiving a guide wire 112 (shown in FIGS. 5–7), used during the implantation procedure. The bone screw head 67 has a cruciform slot 69 for receiving a cruciform screw driver (not shown). The bone screw is preferably fabricated from implant quality stainless steel.

FIGS. 5–8 illustrate a procedure for using the threaded washer of the invention together with a cannulated bone screw, for reduction and fixation of a small bone fracture. Those skilled in the art will recognize that other procedures for implanting the threaded washer, using cannulated or non-cannulated screws, are possible. It will furthermore be understood that the use of the washer is not limited to the use illustrated.

Figure 5:
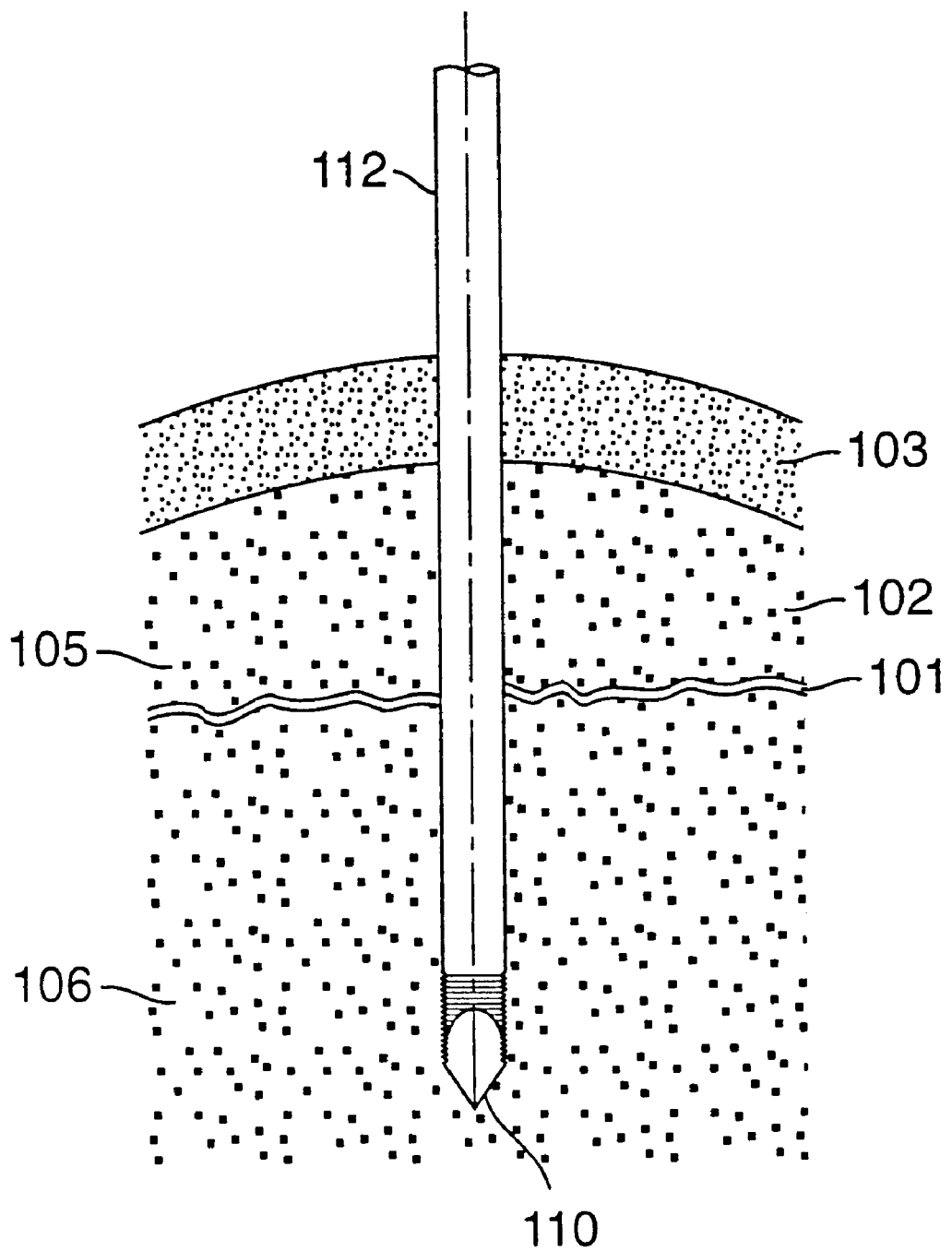
FIG. 5 is a cross-sectional view of a fractured bone after inserting a guide wire according to the invention.

FIG. 5 shows the initial steps in preparing the bone for implantation of the threaded washer and cannulated screw. Fracture plane 101 is shown separating outer fragment 105 from inner fragment 106. At the location selected for the implantation, the fracture plane 101 is within the cancellous region 102 of the bone, beneath the cortex 103.

A self-drilling guide wire 112 is inserted into the bone using a drill (not shown) in an orientation substantially perpendicular to the fracture plane 101. The guide wire has a fluted tip 110 to facilitate drilling. The diameter of the guide wire 112 is chosen to be the proper diameter for the cannulated screw 60; for example, with a 3.0 mm cannulated screw, a 1.1 mm guide wire may be used. The guide wire 112 passes through the cortex 103, through the outer fragment 105, and penetrates the inner fragment 106 sufficiently to permit the thread 61 of the cannulated screw 60 (FIG. 4) to completely engage the inner fragment. A drilling depth gauge (not shown) may be used to insure a proper guide wire depth.

Figure 6:
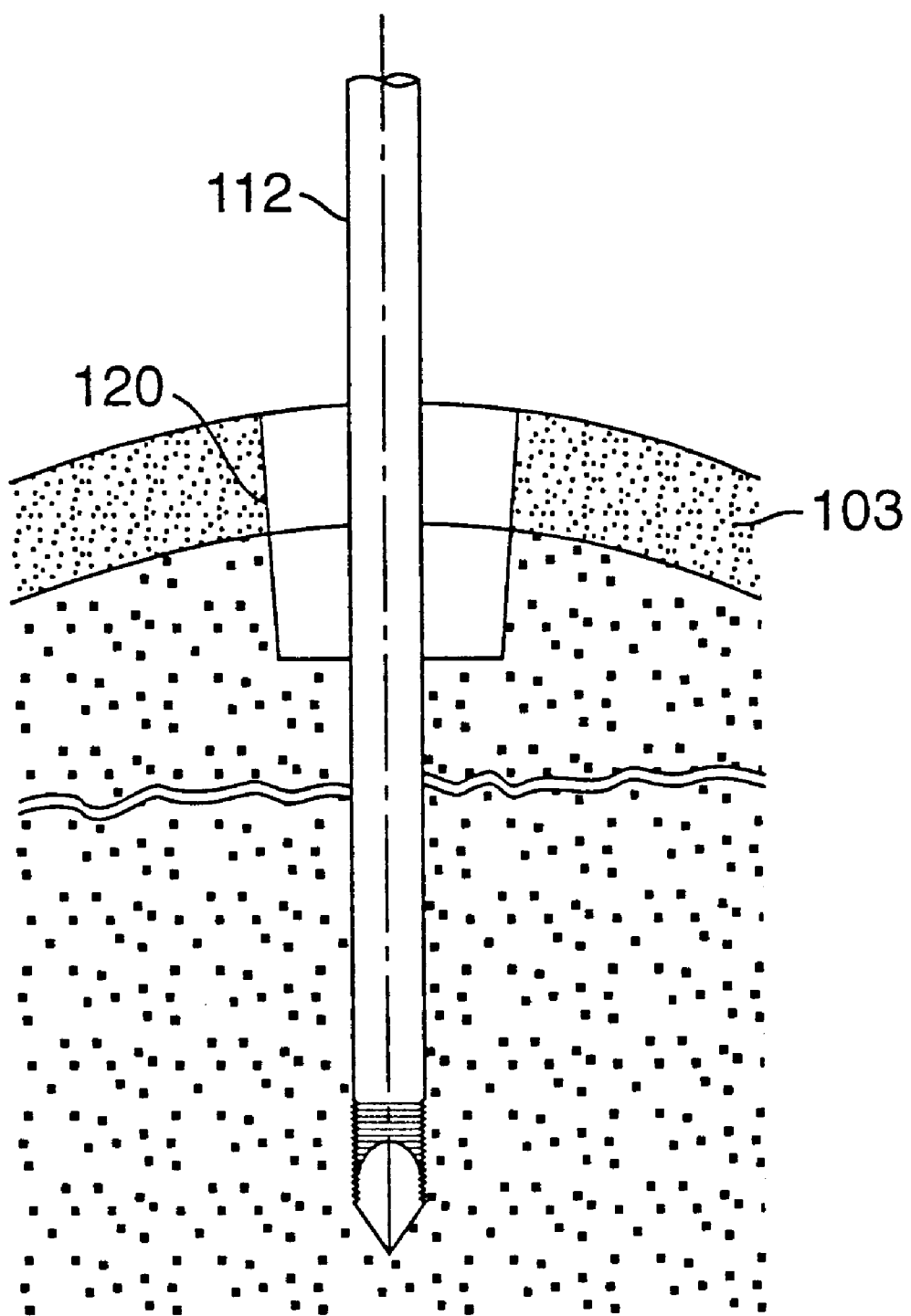
FIG. 6 is a cross-sectional view of a fractured bone after reaming a hole for the threaded washer according to the invention.

As shown in FIG. 6, a tapered counterbore 120 is reamed in a position concentric to the guide wire 112 using a cannulated tapered reamer (not shown). The reamer is guided using the guide wire 112 in the manner known in the art. The depth of the counterbore may be controlled using a gauging mark on the reamer (not shown) that aligns with the outer surface of the cortex 103.

Figure 7:
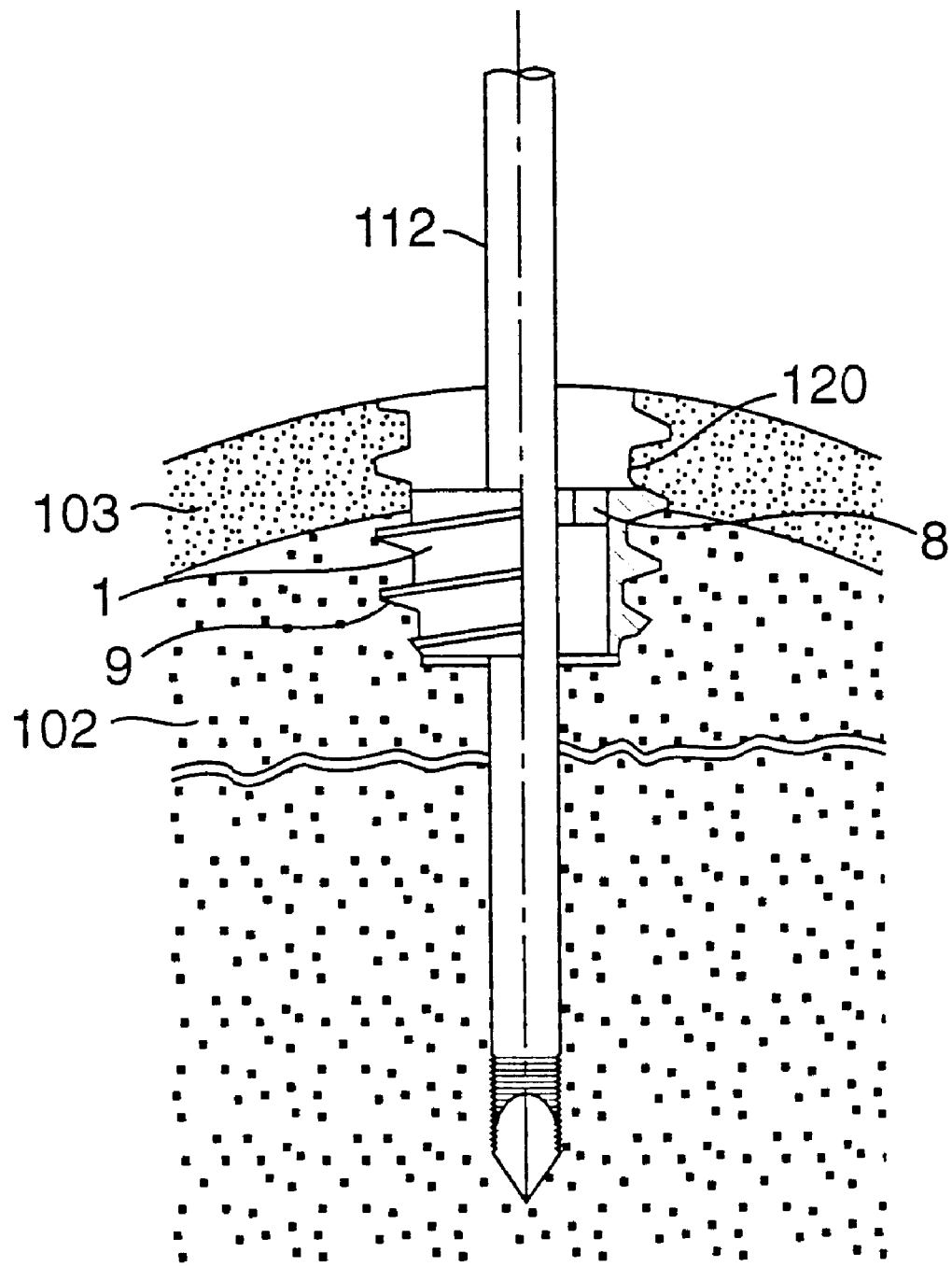
FIG. 7 is a cross-sectional view of a fractured bone after inserting a threaded washer according to the invention.

The threaded washer 1 is installed in the counterbore 120 as shown in FIG. 7. The threaded washer 1 is first assembled over guide wire 112. A cannulated hexagonal driver (not shown) is then assembled over the guide wire 112 above the threaded washer 1 and engaged with the hexagonal socket 8 of the threaded washer. Using the hexagonal driver, the threaded washer is rotated in the counterbore 120, engaging the thread 9 with the bone material. Cutting flutes 14 (FIG. 1) permit the tapered thread 9 to cut through cortex 103 and cancellous bone 102. The washer 1 is rotated until thread 9 is fully engaged in tapered hole 120.

In the embodiment in which the washer 1 is fabricated of a bioabsorbable material, the use of a self-tapping thread with cutting flutes may not be possible. In that case, the counterbore is tapped using a tapered, cannulated tap before implanting the threaded washer.

Figure 8:
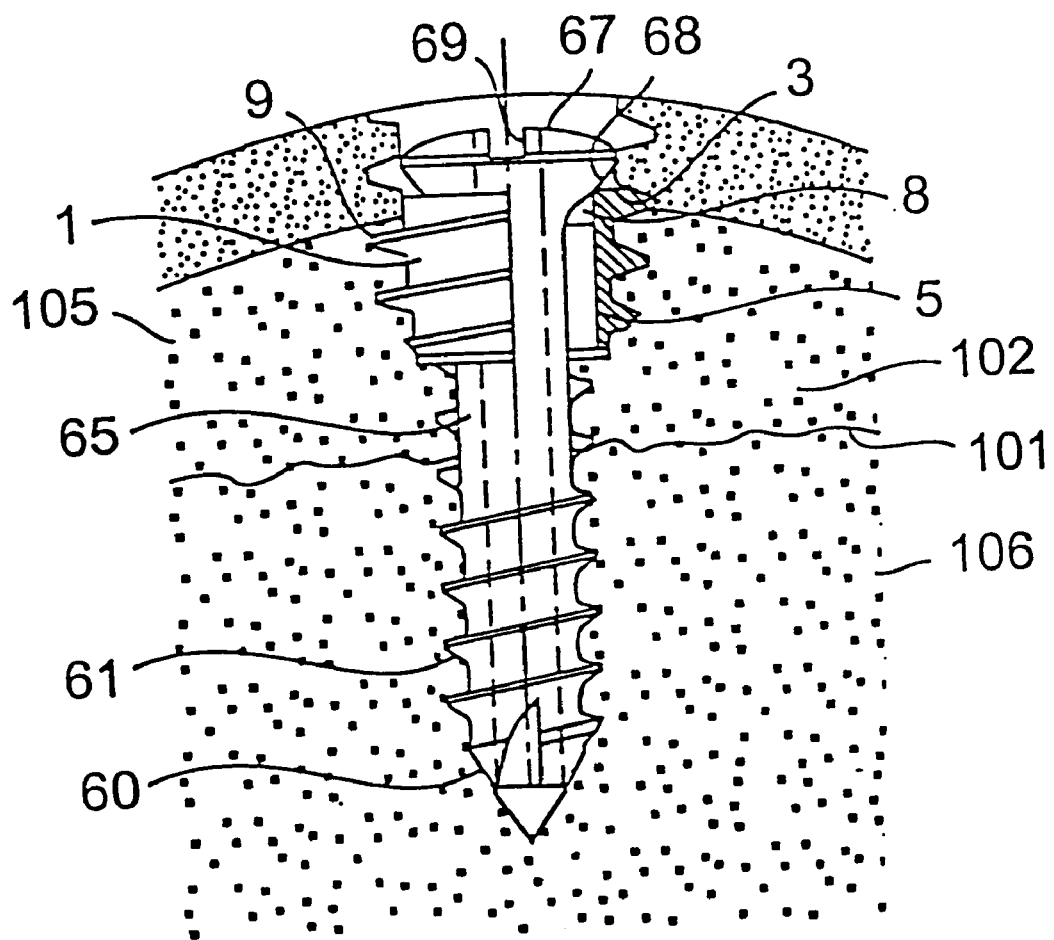
FIG. 8 is a cross-sectional view of a fractured bone after installing and tightening a cannulated screw according to the invention.

FIG. 8 shows the threaded washer and cannulated screw after installation is complete. The cannulated screw 60 is assembled over the guide wire (not shown), and a cannulated cruciform screwdriver (not shown) is then assembled over the guide wire above the cannulated screw and in engagement with the cruciform slot 69 of the cannulated screw. Sliding on the guide wire 112, the cannulated screw is passed through the central bore 5 of threaded washer 1 until screw threads 61 engage the cancellous bone material 102 of the outer fragment 105 surrounding the guide wire. The cruciform screwdriver is then used to rotate the cannulated screw 60 until threads 61 pass through the outer fragment 105 and are entirely engaged in inner fragment 106. The unthreaded shaft portion 65 of the cannulated screw passes through the washer 1 without contact. The shaft portion 65 fully contacts the bone material immediately above and below the fracture plane 101, preventing lateral movement between the inner and outer fragments.

After the cannulated screw 60 is driven into the bone, the undersurface 68 of the screw head 67 contacts the threaded washer 1 at the corners formed by the hexagonal socket 8 and the top edge 3. The fixed depth of threaded washer 1 below the outer surface of the bone ensures that the cannulated screw head 67 will be countersunk to permit joint articulation and prevent soft tissue injury. Further rotation of the cannulated screw 60 draws the inner fragment 106 upward toward the threaded washer 1, reducing the fracture 101. The cannulated screw 60 is then rotated until the proper compressive force is applied across the fracture plane 101.

The compressive force can be increased or decreased without affecting the axial position of the cannulated screw 60 in the outer fragment 105 of the bone. Because the washer thread 9 is tapered, the washer 1 is restrained from advancing due to friction while the bone screw 60 is tightened against the threaded washer 1.

What is claimed is:

1. An apparatus for the fixation of small bone fractures, comprising a washer with a central bore, said central bore having a diameter, and an external tapered thread for engaging an outer bone fragment, and a bone screw having a shaft with a thread with a major diameter less than said diameter of said central bore for engaging an inner bone fragment, and having a screw head larger than said central bore, wherein an upper portion near said screw head of said shaft is disposed within said central bore, and said screw head is disposed exterior said washer and engages a portion of said washer.

2. The threaded washer of claim 1, wherein said external thread has cutting flutes.

3. The apparatus of claim 1, wherein said bone screw is a cannulated bone screw.

4. The apparatus of claim 1, wherein said tapered threads are self tapping.

5. The apparatus of claim 1, wherein said washer is fabricated of a bio-absorbable material.

6. The apparatus of claim 1, wherein said central bore is cylindrical.

7. The apparatus of claim 7 wherein said upper portion near said screw head of said shaft does not have a thread.

8. An apparatus for the fixation of small bone fractures, comprising a washer, said washer having a first pitch, a central bore, said central bore having a diameter, an external tapered thread for engaging an outer bone fragment, and driving means for inserting said washer in the outer bone fragment, and a bone screw disposed within said central bore of said washer, said bone screw having a second pitch, a thread with a major diameter less than said diameter of said central bore for engaging an inner bone fragment, and a screw head larger than said central bore for engaging said washer.

9. The apparatus of claim 8, wherein said the first pitch is the same as the second pitch.

10. The apparatus of claim 8, wherein said driving means comprises a cruciform slot.

11. The apparatus of claim 8, wherein said driving means comprises a hexagonal socket.

12. The apparatus of claim 8, wherein said external tapered thread has a cancellous thread form.

13. A bone implant kit for the fixation of small bone fractures comprising:

a washer, with a central bore having a diameter and an external tapered thread, for engaging an outer bone fragment; and a bone screw, with a threaded shaft having a diameter less than said diameter of said central bore, and a screw head with a diameter larger than said diameter of said central bore, for engaging an inner bone fragment, wherein said washer is adapted to receive said bone screw.

* * * * *